US00PP19992P2

(12) United States Plant Patent
Hatch

(10) Patent No.: US PP19,992 P2
(45) Date of Patent: May 12, 2009

(54) ***OZOTHAMNUS* PLANT NAMED 'SILVER CAPE'**

(50) Latin Name: *Ozothamnus leptophylla*
Varietal Denomination: Silver Cape

(76) Inventor: Lindsey Hatch, 78 Jericho Road, Pukekohe, Auckland (NZ)

( * ) Notice: Subject to any disclaimer, the term of this patent is extended or adjusted under 35 U.S.C. 154(b) by 0 days.

(21) Appl. No.: 11/895,717

(22) Filed: Aug. 27, 2007

(51) Int. Cl.
*A01H 5/00* (2006.01)

(52) U.S. Cl. ..... Plt./226

(58) Field of Classification Search ..... Plt./226, Plt./263.1
See application file for complete search history.

(56) References Cited

PUBLICATIONS

BBC Gardening Plants—Plant Finder Ozothamnus leptphylla [online], [retrieved on Jul. 1, 2008]. Retrieved from the Internet: http://www.bbc.co.uk/gardening/plants/plant_finder/plant_pages/12239.shtml> 2 pp.*

* cited by examiner

*Primary Examiner*—Annette H Para
*Assistant Examiner*—June Hwu
(74) *Attorney, Agent, or Firm*—Mark P. Bourgeois

(57) ABSTRACT

A new cultivar of *Ozothamnus* plant named 'Silver Cape' that is characterized by spiral silver colored leaves, a short internode length and a compact habit.

1 Drawing Sheet

Botanical Classification: *Ozothamnus leptophylla.*
Variety Denomination: 'Silver Cape'.

BACKGROUND OF THE INVENTION

The present invention relates to a new and distinct cultivar of *Ozothamnus* plant botanically known as *Ozothamnus leptophylla* and hereinafter referred to by the cultivar name 'Silver Cape'.

The new cultivar originated from a cross of the male or pollen parent plant an unidentified cultivar of *Ozothamnus leptophylla* and the female or seed parent plant an unidentified cultivar of *Ozothamnus leptophylla.* 'Silver Cape' was selected as a single plant from the progeny of the stated cross by the inventor in a cultivated area of Pukekohe, New Zealand in 2002.

Asexual reproduction by terminal cuttings of the new cultivar 'Silver Cape' was first performed in 2002 in Pukekohe, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Ozothamnus* cultivar 'Silver Cape'.

1. *Ozothamnus* 'Silver Cape' exhibits silver colored foliage.
2. *Ozothamnus* 'Silver Cape' exhibits small internodes.
3. *Ozothamnus* 'Silver Cape' exhibits foliage positioned in a spiral leaf arrangement.
4. *Ozothamnus* 'Silver Cape' grows a compact habit.

The closest comparison cultivars are plants of the parent species *Ozothamnus leptophylla.*

The new cultivar 'Silver Cape' is distinguishable from plants of the species by the following characteristics:

1. 'Silver Cape' has silver colored leaves.
2. 'Silver Cape' has a shorter internode length.
3. 'Silver Cape' has shorter leaves.

BRIEF DESCRIPTION OF THE DRAWING

The accompanying photograph illustrates the distinguishing traits of *Ozothamnus*'Silver Cape'. The plant in the photograph shows an overall view of a 1 year old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Ozothamnus* cultivar named 'Silver Cape'. Data was collected in Cambridge, New Zealand from 1 year old field grown plants. The time of year was Winter in the Southern Hemisphere and the temperature range was 0 to 20 degrees Centigrade during the day and −4 to 12 degrees Centigrade at night. No photoperiodic treatments or growth retardants were used. Color determinations are in accordance with The Royal Horticultural Society Colour Chart 2001 edition, except where general color terms of ordinary dictionary significance are used. The growing requirements are similar to the species. 'Silver Cape' has not been tested under all possible conditions and phenotypic differences may be observed with variations in environmental, climatic, and cultural conditions, however, without any variance in genotype.

Botanical classification: *Ozothamnus leptophylla* 'Silver Cape'.
Use: Ornamental perennial shrub.
Vigor: Semi Vigorous.
Growth rate: 0.4 m per year.
Growth habit: Upright.

Plant shape: Narrowly conical.
Suitable container size: 2 L.
Height: Average 1.2 m in height.
Width: Average 0.6 m in width.
Low temperature tolerance: −12° Centigrade.
High temperature tolerance: 28° Centigrade.
Propagation: Terminal cuttings.
Time to initiate roots in summer: 30 days at 22° C.
Time to initiate roots in winter: 40 days at 22° C.
Time to a rooted cutting or liner in summer: 90 days at 18°–24° C.
Time to a rooted cutting or liner in winter: 90–120 days at 10°–15° C.
Root system: Fine and fibrous.
Lateral Branches:
*Quantity.*—5
*Pinching.*—Pinch at third set of leaves.
*Lateral branch length.*—100 mm.
*Lateral branch diameter.*—2 mm.
*Internode length.*—5 mm.
*Stem shape.*—Rounded.
*Stem aspect.*—Upright.
*Stem strength.*—Strong.
*Stem color.*—N199B with webbed pubescence 196C.
*Pubescence.*—Colored 196C.
Foliage:
*Texture.*—Leathery.
*Quantity of leaves per branch.*—Approximately 100.
*Leaf arrangement.*—Spiral.
*Compound or single.*—Single.
*Leaf shape.*—Oval.
*Leaf apex.*—Obtuse.
*Leaf base.*—Truncate.
*Leaf length.*—Average 3 mm in length.
*Leaf width.*—Average 2 mm in width.
*Pubescence.*—Present on both sides.
*Leaf margin.*—Entire.
*Young leaf color* (*upper surface*).—196C.
*Young leaf color* (*lower surface*).—196C.
*Mature leaf color* (*upper surface*).—N189A.
*Mature leaf color* (*lower surface*).—196C.
*Durability of foliage to stress.*—Good.
Petiole:
*Petiole length.*—0.5 mm.
*Petiole diameter.*—2 mm.
*Petiole color.*—196C.

Flowers:
*Flower arrangement.*—Within capitulum.
*Inflorescence type.*—Capitula arranged in compound cymes.
*Inflorescence height.*—20 mm.
*Inflorescence width.*—15 mm.
*Quantity of flowers per inflorescence.*—9–15 capitula per compound cyme.
*Flower type.*—Tubular disc florets, no ray florets.
*Quantity of flowers per lateral stem.*—15–20 disc florets per capitulum.
*Flowering season.*—Spring to Fall.
*Fragrance.*—Foetid.
*Bud dimensions.*—5 mm. in length and 2 mm. in diameter.
*Bud shape.*—Fusiform.
*Bud color.*—196D.
*Rate of bud opening.*—3 days.
*Flower aspect.*—Upright.
*Flower shape.*—Tubular disc florets.
*Flower dimensions.*—0.8 mm. in diameter and 0.6 mm. in height.
*Self-cleaning or persistent.*—Persistent.
Reproduction organs:
*Stamen number.*—5.
*Anther shape.*—Ensiform.
*Anther dimensions.*—0.5 mm.
*Anther color.*—196D.
*Amount of pollen.*—Low.
*Pollen color.*—196D.
*Pistil number.*—1 in number.
*Pistil dimensions.*—6 mm. in length.
*Stigma shape.*—Bifid, recurving.
*Stigma color.*—196D.
*Style length.*—5 mm.
*Style color.*—194A.
*Ovary color.*—194A.
Seed: 12–20 seeds per capitulum, 1.2 mm in length and 0.5 mm in width, color 199B.
Disease and Insect Resistance: Plants of the new *Ozothamnus* have not been observed for disease or insect resistance.

What is claimed is:

1. A new and distinct variety of *Ozothamnus* plant named 'Silver Cape' as described and illustrated.

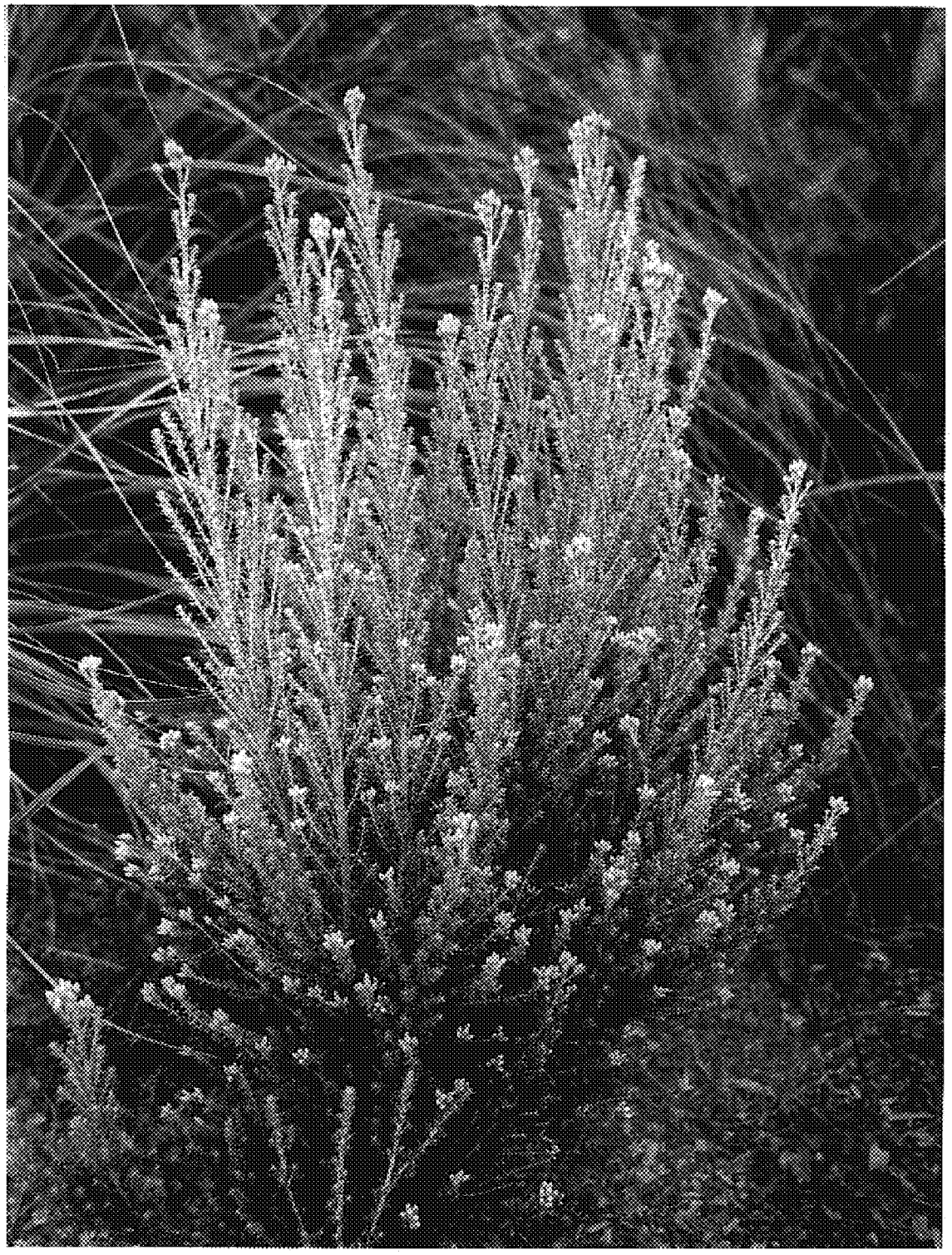

* * * * *